(12) United States Patent
Chung et al.

(10) Patent No.: US 10,894,945 B2
(45) Date of Patent: Jan. 19, 2021

(54) METHODS FOR IMPROVING PROLIFERATION AND STEMNESS OF LIMBAL STEM CELLS

(71) Applicant: CATHOLIC UNIVERSITY INDUSTRY ACADEMIC COOPERATION FOUNDATION, Seoul (KR)

(72) Inventors: So-Hyang Chung, Seoul (KR); Hyun Jung Lee, Seoul (KR)

(73) Assignee: CATHOLIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 217 days.

(21) Appl. No.: 15/463,737

(22) Filed: Mar. 20, 2017

(65) Prior Publication Data
US 2017/0283773 A1    Oct. 5, 2017

(30) Foreign Application Priority Data
Mar. 29, 2016 (KR) .................. 10-2016-0037741

(51) Int. Cl.
*C12N 5/079*    (2010.01)

(52) U.S. Cl.
CPC ...... *C12N 5/0621* (2013.01); *C12N 2501/415* (2013.01); *C12N 2533/30* (2013.01)

(58) Field of Classification Search
None
See application file for complete search history.

(56) References Cited

FOREIGN PATENT DOCUMENTS

| KR | 10-0931887 B1 | 12/2009 | |
| WO | WO-2013184843 A1 * | 12/2013 | ............ C12M 23/04 |

OTHER PUBLICATIONS

Utheim, T.P. et al. 2007. A novel method for preserving cultured limbal epithelial cells. British Journal of Ophthalmology 91: 797-800. specif. p. 797.*
MacDonald, B.T. et al. 2009. Wnt/B-catenin signalling: components, mechanisms, and diseases.Developmental Cell 17: 9-26. specif. pp. 9, 10, 11.*
Ghoubay-Benallaoua, D. et al. 2013. Kinetics of expansion of human limbal epithelial progenitor cells in primary culture of explants without feeders. PLoS ONE 8(12): 1-8. specif. pp. 1, 2.*
Jung et al., "Influences of Control of Wnt Signaling pathway on Efficiency of Proliferation of Limbal Stem Cells" The 113th Annual Meeting of the Korean Ophthalmological Society, three pages, Apr. 11, 2015, with translation 2 pages.
Ebrahimi et al., "Limbal Stem Cells in Review", Journal of Ophthalmic and Vision Research, 2009, vol. 4, No. 1, pp. 40-58.
Jin et al., "The Effects of Wnt Protein on Proliferation and Sternness Maintenance of Corneal Limbal Stern Cells (CLSCs)", J Korean Ophthalmol Soc, 2009, vol. 50, No. 4, pp. 588-593.
Mikhailova et al., "Small-Molecule Induction Promotes Corneal Epithelial Cell Differentiation from Human Induced Pluripotent Stem Cells", Stem Cell Reports, 2014, vol. 2, No. 2, pp. 219-231.

* cited by examiner

*Primary Examiner* — Renee Claytor
*Assistant Examiner* — Sharon M. Papciak
(74) *Attorney, Agent, or Firm* — Vorys, Sater, Seymour & Pease LLP; Mih Suhn Koh

(57) ABSTRACT

Provided are methods for improving the proliferation and stemness of limbal stem cells (LSCs) by adding a Wnt inhibitor to a medium for limbal explant cultures. When human limbal explants are cultured according to the methods, Wnt/β-catenin signaling is inhibited, resulting in improvement of LSC proliferation, and improvement in the stemness of LSCs, and thus the LSCs may be obtained in high yield.

2 Claims, 6 Drawing Sheets

METHODS FOR IMPROVING PROLIFERATION AND STEMNESS OF LIMBAL STEM CELLS

CROSS-REFERENCE TO RELATED APPLICATION

This application claims priority to and the benefit of Korean Patent Application No. 10-2016-0037741, filed on Mar. 29, 2016, the disclosure of which is incorporated herein by reference in its entirety.

The present invention was undertaken with the support of Analysis of the effect of corneal epithelial regeneration with limbal explant epithelial sheets No. HI14C1607 grant funded by the Ministry of Health and Welfare.

BACKGROUND

1. Field of the Invention

The present invention relates to methods for improving the proliferation and stemness of limbal stem cells (LSCs) by adding a Wnt inhibitor to a medium for a limbal explant.

2. Discussion of Related Art

The cornea is the most anterior part of the eye that covers about ⅙ of the area of the anterior surface of the eye and has a size of about 11 mm and generally a thickness of about 0.55 mm, while being thinnest at the center and becoming gradually thicker toward the periphery portions. Also, the cornea is a transparent tissue that has the key functions in light refraction and transmission, and has well-developed nerves, resulting in high sensitivity to foreign matter. The cornea has five layers comprising the corneal epithelium, Bowman's membrane, the corneal stroma, Descemet's membrane and the corneal endothelium, and the normal cornea has no blood vessels, and receives oxygen from the air via tears and nutrients from the aqueous fluid in the anterior chamber behind the cornea and the limbus. It has been reported that, globally, about 4.5 million people are bilaterally blind, and among them, cornea-related diseases lead to blindness in about a million patients.

The survival of corneal epithelial cells is maintained by stem cells present in the limbus, and LSCs are unipotent adult stem cells that can only differentiate into the corneal epithelium. In LSC deficiency (LSCD), the migration of basal corneal epithelial cells onto a surface of the cornea and the migration of corneal epithelial cells on the periphery portions into the center thereof are reduced, and the loss of corneal epithelial cells is thus greater than the proliferation, resulting in a failure in renewal of the corneal epithelium. As a result, conjunctival epithelial cells penetrate onto the cornea through the limbus, which is called "conjunctivalization." Despite a new environment, the conjunctival epithelial cells form corneal vascularization while maintaining a unique phenotype, and thereby a patient has corneal opacity and then becomes blind.

When the cornea has opacity without maintaining its transparency because of external injuries, serious inflammations or congenital causes, even though all of the other functions of the eye as well as optic nerve are normal, a serious visual impairment is made. When such opacity is difficult to be treated with drugs or laser, the cornea needs to be excised and replaced with a clear cornea from a donor eyeball to facilitate light transmission into the eyes, and this surgical procedure is referred to as corneal transplantation.

In the case of such blindness caused by lesions in the cornea itself, visual recovery can be expected by corneal transplantation, whereas in the case of the conjunctivalization and opacity of the cornea triggered by LSCD, visual recovery can be expected only by successful transplantation of LSCs. Therefore, since this case has no options other than stem cell transplantation, the opacity of the cornea and blindness triggered by LSCD are classified as intractable diseases.

LSCD is a disease triggered by deficiency of LSCs for constant renewal of the corneal epithelium, resulting from a wide range of damage to the limbus due to congenital causes or acquired causes such as external injuries, inflammations, UV-induced damage, surgical damage, complications caused by contact lens wearing and systemic diseases, and LSCD patients are constantly increasing due to an increase in prevalence and severity of xerophthalmia and the expanded use of toxic eye drops, as well as the causes mentioned above.

As a method for treating LSCD, autologous or homologous limbal tissue transplantation has been used. In the case of autologous limbal tissue transplantation, a method for transplanting the same size of limbal tissue which has been taken from the other eye is used, which, however, has a risk of development of LSCD in the donor eye. Meanwhile, in the case of the transplantation of homologous limbal tissues donated from a dead body, patients are suffering from side effects caused by the constant use of a systemic immunosuppressant, and the death of a significant amount of stem cells frequently occurs due to limbal graft rejection even when the systemic immunosuppressant is used. As described above, while LSCD is constantly increasing, a proper treating method which is effective for patients with less complications has not been developed yet.

Particularly, LSCs present in the limbus, which is the contact part between the cornea and the conjunctiva, play an important role in the maintenance, repair and renewal of the corneal epithelium. However, the isolation of the LSCs is very difficult because the number of the LSCs are less than 1% and, the LSCs are embedded in a basal membrane of the multilayer limbal epithelium. To solve such a problem, conventionally, methods for culturing of multipotent stem cells isolated from the corneal limbus have been reported (Korean Patent No. 10-0931887), but there is no efficient method for clinical and practical uses.

Therefore, in order to increase a successful treatment rate and therapeutic effects, the development of an effective method for ensuring LSCs in a large amount by stimulating the proliferation of LSCs and constantly maintaining a self-renewal capacity is needed.

SUMMARY OF THE INVENTION

As a result of the study on a method for ensuring LSCs in a large amount to solve the conventional problems, the inventors identified that when a Wnt inhibitor is added to a medium under culture conditions for a human limbal explant, the proliferation and stemness of LSCs are improved, and the differentiation of LSCs is inhibited, and on the basis of this result, the present invention has been completed.

Therefore, the present invention is directed to providing a method for improving the proliferation of LSCs in a human limbal explant culture.

Also, the present invention is directed to providing a method for improving the stemness of LSCs in a human limbal explant culture.

However, technical problems to be solved in the present invention are not limited to the above-described problems, and other problems which are not described herein will be fully understood by those of ordinary skill in the art from the following descriptions.

According to one aspect, the present invention provides a method for improving the proliferation of LSCs, which includes:

(a) immersing a human limbal explant in a medium; and
(b) adding a Wnt inhibitor to the medium.

According to another aspect, the present invention provides a method for improving the sternness of LSCs, which includes:

(a) immersing a human limbal explant in a medium; and
(b) adding a Wnt inhibitor to the medium.

In one exemplary embodiment of the present invention, the Wnt inhibitor may be N-(6-Methyl-2-benzothiazolyl)-2-[(3,4,6,7-tetrahydro-4-oxo-3-phenylthieno[3,2-d]pyrimidin-2-yl)thio]-acetamide (IWP2).

In another exemplary embodiment of the present invention, the Wnt inhibitor may reduce an amount of β-catenin in cells.

In still another exemplary embodiment of the present invention, the limbal explant may be prepared by placing the epithelial part of a limbal tissue face-up on a polyester membrane insert.

In yet another exemplary embodiment of the present invention, the method may improve a colony forming efficiency (CFE) of LSCs.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 2a shows the outgrowth cultures of limbal explants stained with Commassie blue R 250. FIGS. 2b to 2d are quantified results for outgrowth areas, cell yields, and cell densities (cells/mm$^2$) of the outgrowth cultures of limbal explants, respectively;

DETAILED DESCRIPTION OF EXEMPLARY EMBODIMENTS

Figure 1:
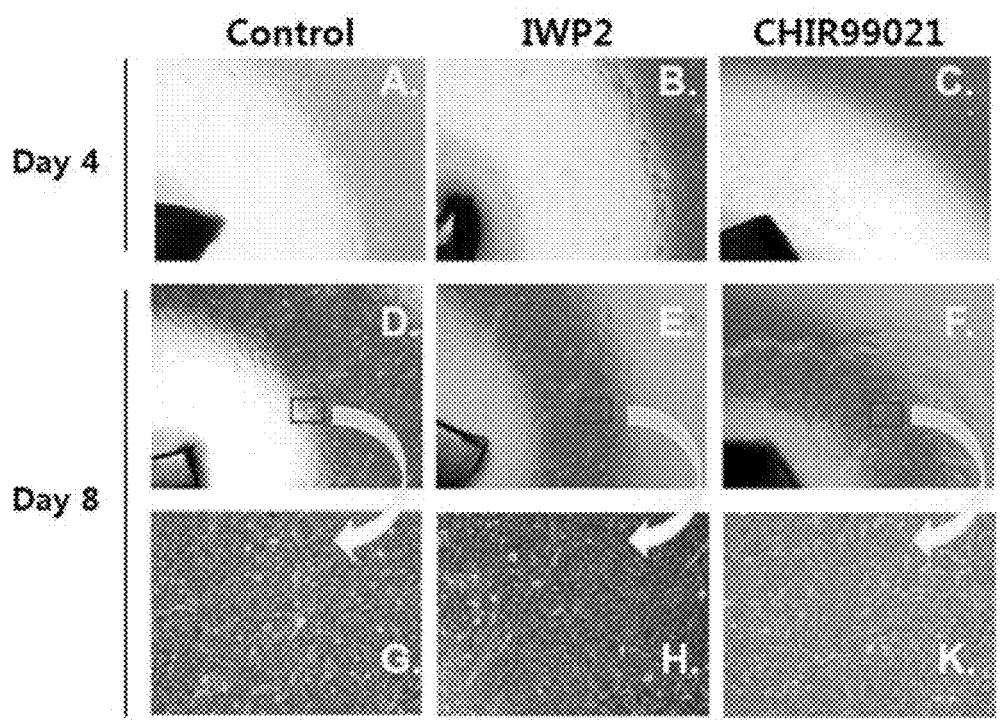
FIG. 1 shows outgrowth proliferation rates of an explant observed under a phase contrast microscope on day 4 and day 8, after addition of the Wnt inhibitor IWP2 or the Wnt signaling agonist CHIR99021, as a glycogen synthase kinase 3 (GSK3) inhibitor, to a medium for a human limbal explant.

As a result for the study on searching for a method for ensuring LSCs in a large amount to solve the conventional problems, the inventors identified that the addition of a Wnt inhibitor to a medium under culture conditions for a human limbal explant cultures leads to the stimulation of cell proliferation on the limbal explant cultures per unit area, an increase in ratio of LSCs, and improvement of sternness and inhibition of differentiation of LSCs, and on the basis of this, the present invention has been completed.

Therefore, the present invention provides a method for improving proliferation of LSCs, which includes:

(a) immersing a human limbal explant in a medium; and
(b) adding a Wnt inhibitor to the medium.

The term "LSC" used herein refers to a unipotent adult stem cell present in the limbus and capable of only differentiating into the corneal epithelium, and is also called a corneal epithelial progenitor cell.

In the step (a), a limbal explant may be prepared by placing the epithelial part of a human limbal tissue face-up on a polyester membrane insert. Afterward, the limbal explant may be cultured for 10 to 20 days, preferably, about 15 days, in a supplemented hormonal epithelial medium (SHEM) with DMEM/F-12, a human recombinant epidermal growth factor (EGF), phosphoethanolamine and insulin-transferrin-selenium (ITS), which is replaced with a fresh medium every 72 hours. However, types of a membrane and a medium are not limited thereto, as long as they are suitable for the limbal explant cultures.

In the step (b), the Wnt inhibitor inhibits Wnt signaling by inactivation of an acetyltransferase of the porcupine protein involved in acylation of a Wnt protein, thereby reducing an amount of β-catenin in cells. The Wnt inhibitor may be added to the medium in a concentration of 5 to 15 μM, and preferably, 10 μM when cells are initially proliferated on the limbal explant cultures. Here, a Wnt inhibitor that can be used herein may be IWP2. However, the present invention is not limited thereto, any material that can inhibit Wnt/β-catenin signaling by reducing the amount of β-catenin in cells may be suitably selected by those of ordinary skill in the art.

The term "Wnt/β-catenin signaling" used herein is also referred to as a canonical Wnt pathway which plays an important role in generation and development of organs of the body through regulation of axis patterning, cell fate determination, cell proliferation and cell migration during embryonic development, and is involved in maintenance of tissue homeostasis and tissue renewal even in an adult. When β-catenin is accumulated in the cytoplasm, it is translocated into the nucleus and acts as a transcriptional coactivator of a transcription factor to regulate gene expression. When there is no Wnt signal, degradation of the β-catenin is mediated by a complex consisting of axin, adenomatosis polyposis coli (APC), protein phosphatase 2A (PP2A), glycogen synthase kinase 3 (GSK3) and casein kinase 1α (CK1α). However, when Wnt binds to Fz and LRP5/6 receptors, the function of the complex is inhibited, and thus the β-catenin is not degraded but accumulated in the cytoplasm.

The inventors demonstrated that LSC proliferation can be improved by inhibition of Wnt/β-catenin signaling under culture conditions for a limbal explant cultures.

In an exemplary embodiment of the present invention, as a result of cell culturing by adding the Wnt inhibitor IWP2 or the Wnt signaling agonist CHIR99021, as a GSK3 inhibitor, to a medium for a limbal explant cultures, when Wnt/β-catenin signaling was inhibited by the addition of IWP2, outgrowth proliferation, an outgrowth area and cell yields of the explant were similar to those of the control, but a cell density was significantly higher than that of the control. Contrarily, when the degradation of the β-catenin by GSK3 was inhibited by the addition of CHIR99021, and the Wnt/β-catenin signaling was thus activated, it was identified that the outgrowth proliferation on the limbal explant cultures was remarkably reduced (refer to Example 2).

In another exemplary embodiment of the present invention, when explant outgrowth cells cultured under the same culture conditions as Example 2 were harvested and $JC1^{low}$ side population of LSCs was measured, it was identified that an IWP2-treated group showed the highest JC1 exclusion cell cohort ($JC1^{low}$), whereas a CHIR99021-treated group showed the lowest JC1 exclusion cell cohort (refer to Example 3).

In still another exemplary embodiment of the present invention, when IWP2 or CHIR99021 was added to each medium under culture conditions for a human limbal explant cultures or isolated limbal epithelial cell cultures, it was identified that, under the conditions for the limbus-derived single cell culture, the suppression of the Wnt/β-catenin signaling did not show the same result as that under the conditions for the explant culture, and the viable cell counts were remarkably decreased in all groups, compared with the group under the conditions for the limbal explant culture (refer to Example 6).

Consequently, it was identified that the method for adding the Wnt inhibitor capable of inhibiting the Wnt/β-catenin signaling to a medium during the culture of a human limbal explant can be used to improve the proliferation of LSCs and obtain LSCs in high yield.

In yet another exemplary embodiment of the present invention, as a result of western blot analysis performed on explant outgrowth cells after being cultured under the same conditions as Example 2, it was identified that expression of the LSC markers p63α and ABCG2 increased and the differentiation marker Krt3 was barely expressed in the cells of a IWP2-treated group, whereas expression of the differentiation marker Krt3 increased in a CHIR99021-treated group (refer to Example 4). Also, according to analysis of a CFE, it was identified that CFE was remarkably increased in the cells of the IWP2-treated group, but the opposite result was shown in the CHIR99021-treated group (refer to Example 5).

In addition, the inventors demonstrated that the inhibition of the Wnt/β-catenin signaling under the culture conditions for a limbal explant can lead to the improvement in LSC proliferation and the sternness of the proliferated LSCs.

Consequently, the inventors identified that the sternness of LSCs is improved by inhibiting the Wnt/β-catenin signaling under the culture conditions for a limbal explant Therefore, as another aspect of the present invention, the present invention provides a method for improving the sternness of LSCs, which includes:
(a) immersing a human limbal explant in a medium; and
(b) adding a Wnt inhibitor to the medium.

Hereinafter, exemplary examples will be provided to help in understanding of the present invention. However, the following examples are merely provided to facilitate understanding of the present invention, and the scope of the present invention is not limited to the following examples.

EXAMPLES

Example 1. Preparation and Methods for Experiment 1-1. Preparation of Limbal Tissue Post-keratoplasty discards of human corneal-limbal tissues from unidentifiable cadavers were obtained from an eye bank, and in the experiment, only corneal limbal tissue (1) isolated from a donor ranging in age from 30 to 65 years at death, (2) isolated within 12 hours after the death of the donor, (3) stored in Optisol (Bausch & Lomb, USA) less than 48 hours after the tissue harvest, and (4) isolated from a donor who had not been infected by human immunodeficiency virus (HIV), hepatitis B or C virus, Epstein-Barr virus, or syphilis was used.

The corneal limbal tissue satisfying the above-described conditions was splitted into 8 equal quarters using a surgical instrument on a horizontal sterile-air-flow hood, and the conjunctival edge of each quarter was immersed shortly in 1% trypan blue (Sigma, USA) to stain conjunctival stroma, and all remnants of conjunctiva were carefully removed using conjunctival scissors. Afterward, a sclera tissue was trimmed away, and then each limbal strip was prepared after being cut to a thickness of 0.5 mm using a sharp blade.

1-2. Culture of Limbal Explant

First, a 0.4-μm pore polyester membrane insert (Costar, NY) with a diameter of 25 mm was put into a 6-well plate, and pre-equilibrated overnight cultured in a supplemented hormonal epithelial medium (SHEM). The SHEM was composed of 950 ml of Dulbecco's modified minimal essential medium (DMEM)/F-12 medium in which DMEM and Ham F12 are mixed in a ratio of 1:1, 50 ml of fetal bovine serum (FBS), 5 ng of a human recombinant epidermal growth factor (EGF), 28 mg of phosphoethanolamine, 1x insulin-transferrin-selenium (ITS, Gibco), and 1× penicillin-streptomycin (Gibco). Afterward, the limbal tissue cut into 8 sections with a length of 4 mm according to the method described in Example 1-1 was put on a polyester membrane to dispose an epithelial part face-up, and cultured under an air-liquid interface condition. After 72 hours of culturing, the presence of an encircling island of outgrowth cells were confirmed, and then the medium was replaced with a fresh medium that just covered a surface of the explant, every 72 hours. Here, the cells were cultured with 10 μM of the Wnt inhibitor (IWP2) or 3 μM of the GSK3 inhibitor (CHIR99021), and then experiments that will be described below were performed.

1-3. Culture of Human Limbal Epithelial Cells

The limbal tissue divided according to the method described in Example 1-1 was treated with 2 mg/ml Dispase II (Roche, Indianapolis, Ind.) diluted with keratinocyte medium (KSFM; Invitrogen, Carlsbad, Calif.) and overnight cultured at 4° C. Afterward, a limbal epithelium layer was gently sloughed off from its stromal base under the dissecting microscope, the epithelium layer was treated with TrypLE (GIBCO, Denmark) and cultured for 10 minutes, and then triturated with a pipette to generate a single cell suspension. These cells were seeded into a 25T flask coated with human type I collagen (PureCol$^R$, Biomatrix, SanDiego, Calif.) to be dispensed at a density of 2×10$^5$ cells/flask, and cultured in Cnt50 medium (Cell-N-Tec, Bern, Switzerland) complemented with bovine pituitary extract for up to 2 weeks.

1-4. Flow Cytometry

In order to determine a relative cell size and ABCG2 efflux activity, cells from limal explant outgrowth cultures were harvested by treatment with trypsin, the collected cells were seeded in 6-well plates at a cell density of $2 \times 10^4$/well, treated with 250 nM JC1 dye and incubated for 45 minutes. Afterward, the cells were detached again by trypsin treatment and diluted with FACS buffer to perform FACS analysis. JC1 is a dye binding to mitochondria in cells, efflux of the JC1 dye from cells in a side population strongly expressing ATP-binding cassette sub-family G member 2 (ABCG2) results in inhibition of mitochondria staining. Therefore, flow cytometry was performed on the cells treated with the JC1 dye using a FACS Calibur (BD Biosciences) at an emission wavelength of 531(green)/585 (orange), and the side population ($JC1^{low}$) that was not stained with JC1 was measured.

1-5. Western Blot Analysis

Limbal explant outgrowth cells were washed with PBS, and lysed with a lysis buffer containing phosphatase inhibitor cocktail 2 (Sigma-Aldrich) and protease inhibitor cocktail (Roche Diagnostics). A lysate was boiled with a sample-loading buffer for 10 minutes and then centrifuged, resulting in isolation of a supernatant containing proteins in the cells, and a protein concentration was quantified using a BCA Protein Assay kit (Thermo Fisher Scientific, Rockford, Ill.). Afterward, equal amounts of protein in cell lysates were separated by 10% SDS-polyacrylamide gel electrophoresis (SDS-PAGE) under reducing conditions and electro-transferred to a PVDF membrane (Millipore, Billerica, Mass.). Afterward, The membrane was blocked with 5% skim milk in PBS containing 0.1% Tween 20, incubated at 4° C. for 18 h with primary mouse monoclonal antibodies (Abs) recognizing, β-catenin (BD Biosciences), ABCG2 (Abcam), Krt3 (Abcam) or a rabbit polyclonal antibody recognizing p63α (Abcam). After the washes, the membrane was incubated with a horseradish peroxidase-binding anti-mouse or anti-rabbit secondary antibody at room temperature for 1 hour. The membrane incubating with the secondary antibody was washed with 0.1% Tween 20-added PBS three times, treated with an ECL solution (Amersham Biosciences, Sweden) as a chemiluminescence reagent and developed, thereby analyzing an expression level of a protein to be observed. Also, to correct protein levels of the samples, a mouse monoclonal anti-β-actin primary antibody reacted with the membrane, and subsequent procedures were the same as described above.

1-6. Colony Forming Efficiency Assay

Cells harvested from explant outgrowth cultures by trypsinization, seeded in a 6-well plate coated with human type I collagen (PureCol$^R$, Biomatrix, San Diego, Calif.) to be dispensed at a density of 100 cells/cm$^2$, and then cultured in the presence of Cnt50 (Cell-N-Tec, Bern, Switzerland). Cnt20 has been previously shown to preserve proliferative capacity, colony forming efficiency (CFE) and stem cell-like phenotype of human corneal epithelial cell. After the cells were seeded, a medium was replaced on day 4, 7, 10 or 13, and cultured for up to day 14, cells were fixed in cold methanol, and stained with Commassie blue R 250 to observe colony formation.

Example 2. Comparative Analysis of Explant Outgrowth Proliferation Ability by Regulation of Wnt/β-Catenin Signaling in Limbal Explant Cultures To identify effects of the Wnt/β-catenin signaling on the limbal explant outgrowth cultures, cells were cultured by adding 10 µM of the Wnt inhibitor IWP2 or 3 µM of the Wnt signaling agonist CHIR99021 as a GSK3 inhibitor to a medium under the culture conditions for a human limbal explant cultures according to the methods described in Examples 1-1 and 1-2, and explant outgrowth proliferation was observed using a phase contrast microscope on day 4 and 8.

The Wnt inhibitor IWP2 inhibited the Wnt signaling through inactivation by inhibiting an acetyltransferase activity of the porcupine protein involved in acylation of a Wnt protein, resulting in inhibition of Wnt/β-catenin signaling. Meanwhile, the GSK3 inhibitor CHIR99021 inhibited GSK3, which is involved in degradation of the β-catenin protein in cells, thereby increasing a level of the β-catenin in the cells and thus activating the Wnt/β-catenin signaling.

As a result of culturing the limbal explant by adding IWP2 or CHIR99021 to a medium according to the above-described method, as shown in FIG. 1, outgrowth proliferation rates of the explant were the highest in the control, and sequentially decreased in the IWP2-treated group and the CHIR99021-treated group.

Figure 2A:
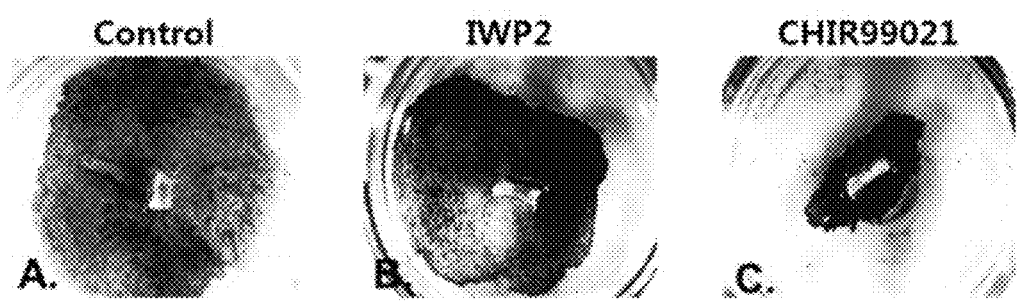
FIGS. 2a to 2d show results of comparing the outgrowth proliferation of limbal explants cultured after addition of the Wnt inhibitor IWP2 or the Wnt signaling agonist CHIR99021, as a GSK3 inhibitor, to each medium for a human limbal explant, where
Figure 2B:
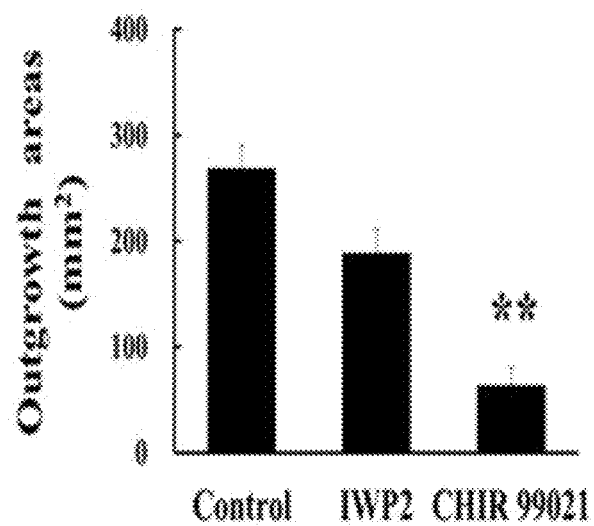

Subsequently, when the limbal explant outgrowth was stained with Commassie blue R 250 and observed with the naked eye, as shown in FIG. 2a, the stained outgrowth areas were subsequently increased in the control, the IWP2-treated group and CHIR99021-treated group. According to the quantitative result shown in FIG. 2b, the CHIR99021-treated group showed a smaller area, which is statistically significant (**P<0.01).

Figure 2C:
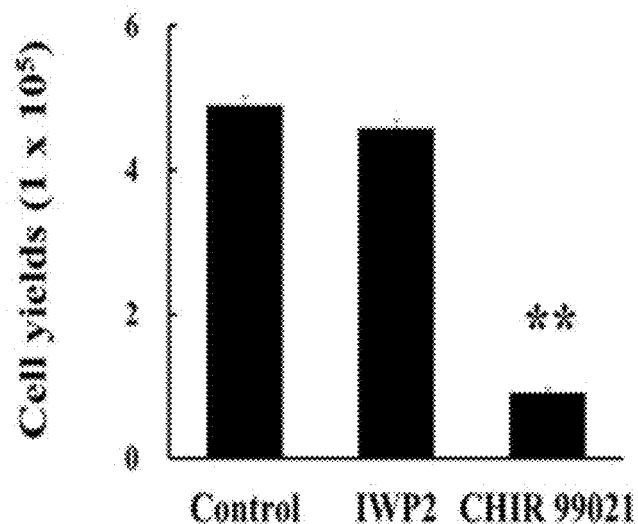
Figure 2D:
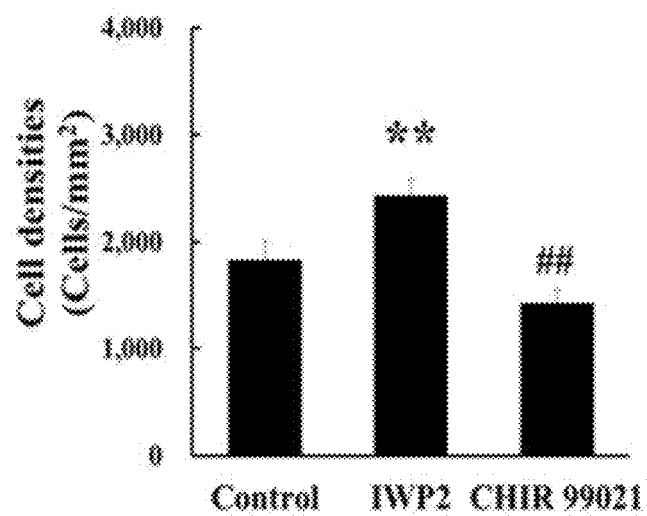

In addition, cells were harvested by treating the limbal explant cultures with trypsin, stained with a 0.4% trypan blue solution, and cell yields were measured using a hemocytometer and then cell densities were quantitatively analyzed. As a result, as shown in FIGS. 2c and 2d, there was no difference in cell yields between the normal control and the IWP2-treated group, and the cell yield was significantly decreased in the CHIR99021-treated group. However, the IWP2-treated group showed the highest cell density (**P<0.01, ##P<0.05).

Consequently, it can be seen that when the Wnt/β-catenin signaling was activated during the limbal explant culture, the explant outgrowth proliferation was remarkably decreased, whereas when the Wnt/β-catenin signaling was inhibited, the cell density was significantly increased.

Example 3. Comparative Analysis of LSC Ratio by Regulation of Wnt/β-Catenin Signaling in Limbal Explant Cultures In order to identify effects of the Wnt/β-catenin signaling on LSCs present in the explant during the limbal explant culture, cells were cultured by adding 10 µM of the Wnt inhibitor IWP2 or 3 µM of the GSK3 inhibitor CHIR99021 to a medium for a human limbal explant cultures according to the method described in Examples 1-1 and 1-2 and then subjected to flow cytometry according to the method described in Example 1-4, resulting in detection of the side population of $JC1^{low}$ cells in the explant cultures.

Figure 3:
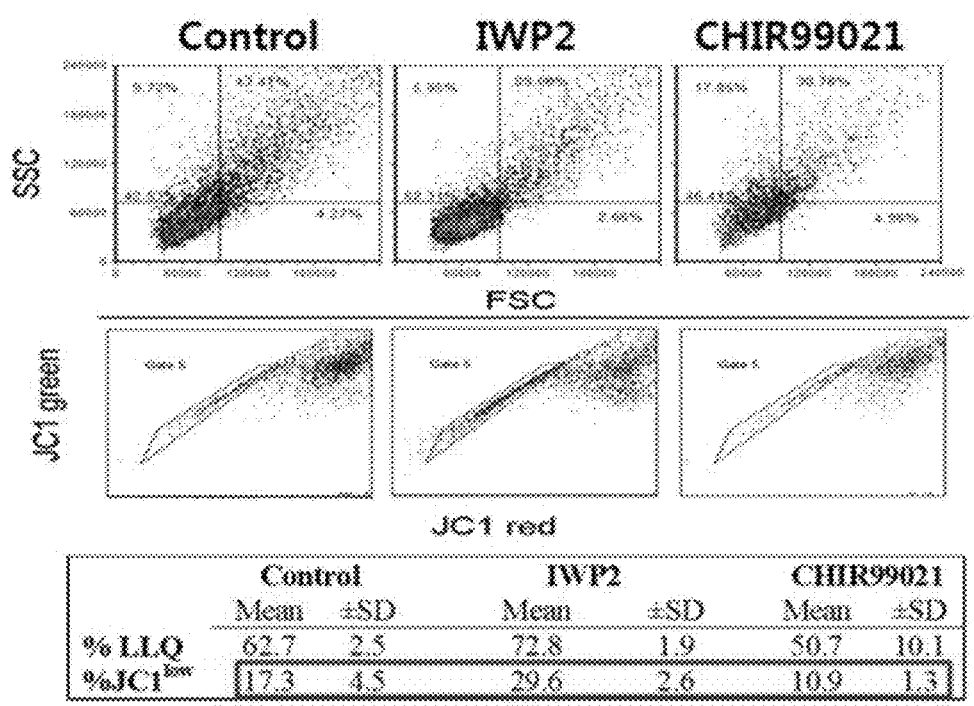
FIG. 3 shows results of comparing ratios of LSCs in limbal explant outgrowth cultures using Flow Cytometry, by measuring a JC1$^{low}$ side population after culturing by adding the Wnt inhibitor IWP2 or the Wnt signaling agonist CHIR99021, as a GSK3 inhibitor, to a medium for a human limbal explant. In the graphs, Y-axis is SSC (Side Scatter) parameter, and X-axis is FSC (Forward Scatter) parameter.

As a result, as shown in FIG. 3, it was identified that the explant cultured by IWP2 treatment showed the highest JC1 exclusion cell cohort ($JC1^{low}$), which was 29.6±2.6%, and the CHIR99021-treated group showed the lowest JC1 exclusion cell cohort, which was 10.9±1.3%. Also, the explant cultured by IWP2 treatment showed the highest percentage in a lower left quadrant (LLQ) exhibiting characteristics of stem/precursor somatic cells, which was 72.8±1.9%, and the CHIR99021-treated group showed the lowest percentage in a LLQ, which was 50.7±10.1%.

From the above results, it was seen that, when the Wnt/β-catenin signaling was inhibited during the limbal explant culture, the percentage of LSCs in a LLQ was increased.

Example 4. Confirmation of Regulation of LSC Differentiation by Regulation of Wnt/β-Catenin Signaling in Limbal Explant Cultures To identify effects of the Wnt/β-catenin signaling on LSC differentiation during the limbal explant culture, expression levels of the LSC markers p63α and ABCG2, and the differentiation marker Krt3 protein in the explant outgrowth cells were detected by western blot analysis according to the method described in Example 1-5.

Figure 4:
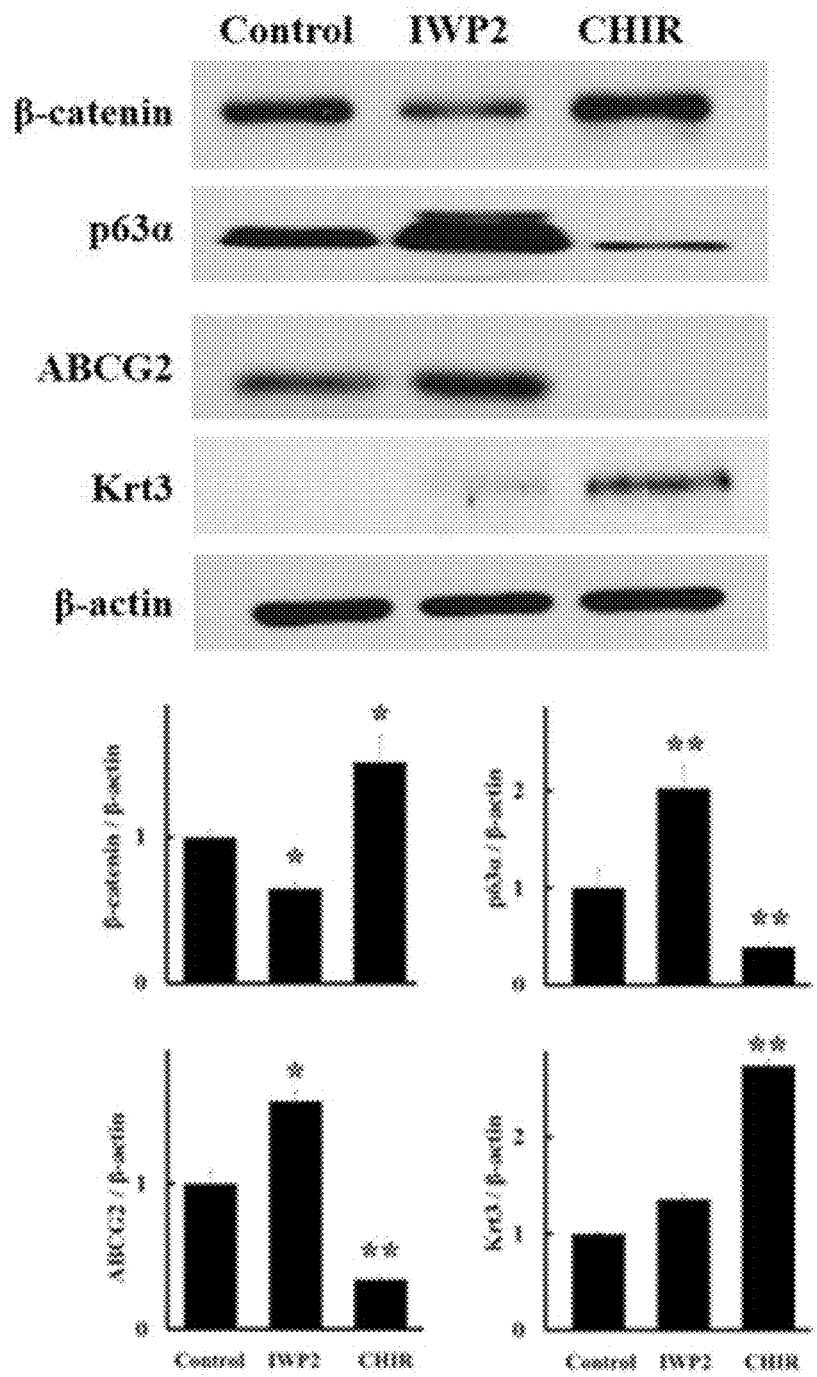
FIG. 4 shows protein expression levels of LSC markers (p63α and ABCG2) and a differentiation marker (Krt3) in limbal explant outgrowth cultures, detected by western blot analysis after cells are cultured by adding the Wnt inhibitor IWP2 or the Wnt signaling agonist CHIR99021, as a GSK3 inhibitor, to a medium for a human limbal explant.

As a result, as shown in FIG. 4, in the IWP2-treated explant outgrowth cells, protein expression of LSC markers p63α and ABCG2 was remarkably increased, compared with that in the control. However, in the CHIR99021-treated explant outgrowth cells, expression levels of the LSC markers p63α and ABCG2 were remarkably decreased, compared with that in the control and expression of the differentiation marker Krt3 was increased (*P<0.05, **P<0.01).

From the above-described results, it can be seen that, during the limbal explant culture, when the Wnt/β-catenin signaling was inhibited, stemness was increased and differentiation was inhibited, whereas when the Wnt/β-catenin signaling was activated, LSC differentiation was stimulated.

Example 5. Comparative Analysis of CFE by Regulation of Wnt/β-Catenin Signaling in Limbal Explant Cultures In order to identify effects of the Wnt/β-catenin signaling on the CFE of explant outgrowth cells during limbal explant culture, limbal explant were cultured according to the methods described in Examples 1-1 and 1-2, and CFE of the control, the IWP2-treated group and the GSK3 inhibitor-treated group was compared according to the method described in Example 1-6.

Figure 5:
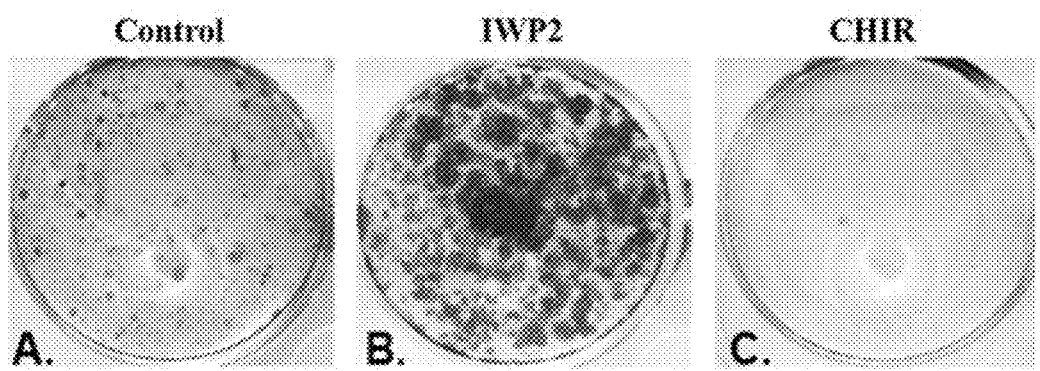
FIG. 5 shows the results of comparing the colony forming efficiency (CFE) of cells harvested from outgrowth cultures of limbal explant after addition of the Wnt inhibitor IWP2 or the Wnt signaling agonist CHIR99021, as a GSK3 inhibitor, to a medium for a human limbal explant.

As a result, as shown in FIG. 5, it was identified that IWP2-treated limbal explant outgrowth cells showed a remarkably higher CFE than those in the control. However, cells of the CHIR99021-treated group barely formed colonies, and showed a remarkably lower CFE than those of the control.

From the above-described results, it was seen that, during the limbal explant culture, when the Wnt/β-catenin signaling was inhibited, the explant outgrowth cells were increased in CFE, whereas when the Wnt/β-catenin signaling was activated, the cells were remarkably decreased in CFE.

Example 6. Comparative Analysis of Effects of Wnt/β-Catenin Signaling According to Methods for Culturing Limbal Tissues 6-1. Measurement of LSC Ratio According to Examples 2 to 4, it was identified that, in the limbal explant culture, the Wnt/β-catenin signaling is involved in the stimulation of explant outgrowth proliferation per unit area, and stemness improvement and differentiation inhibition of LSCs. Accordingly, an experiment was conducted to confirm whether the same effects as described above would be obtained, even when limbal epithelial cells were dissociated according to the method described in Example 1-3, and cultured as single cells. To this end, the limbal explant outgrowth cells according to the method described in Example 1-2 and the cells proliferated from the limbal epithelial cells according to the method described in Example 1-3 were harvested, and each type of cells was subjected to FACS analysis to measure a $JC1^{low}$ ratio.

As a result, as will be shown in Table 1 below, it was identified that, contrary to the results obtained under the culture conditions for the limbal explant cultures, when the limbal epithelial cells derived from the limbal tissue were cultured by single cell culture, the $JC1^{low}$ ratio decreased in order of the CHIR99021-treated group, the control, and the IWP2-treated group.

TABLE 1

|  |  | Control | | IWP2 | | CHIR99021 | |
| --- | --- | --- | --- | --- | --- | --- | --- |
|  |  | Mean | ±SD | Mean | ±SD | Mean | ±SD |
| Epithelial cells | Cell count (1 × 10⁵) | 5.7 | 0.5 | 4.1 | 0.7 | 7.0 | 0.8 |
|  | % $JC1^{low}$ | 14.5 | 1.9 | 9.8 | 1.9 | 23.9 | 2.1 |
| Explant | Cell count (1 × 10⁵) | 4.8 | 0.2 | 4.3 | 0.2 | 0.8 | 0.1 |
|  | % $JC1^{low}$ | 18.1 | 2.3 | 27.9 | 3.1 | 6.4 | 1.2 |

6-2. Measurement of Cell Yield

Based on the results of Example 6-1, cells cultured by the same method as described above were recovered to measure viable cell counts, yields of the limbal epithelial cells were measured.

Figure 6:
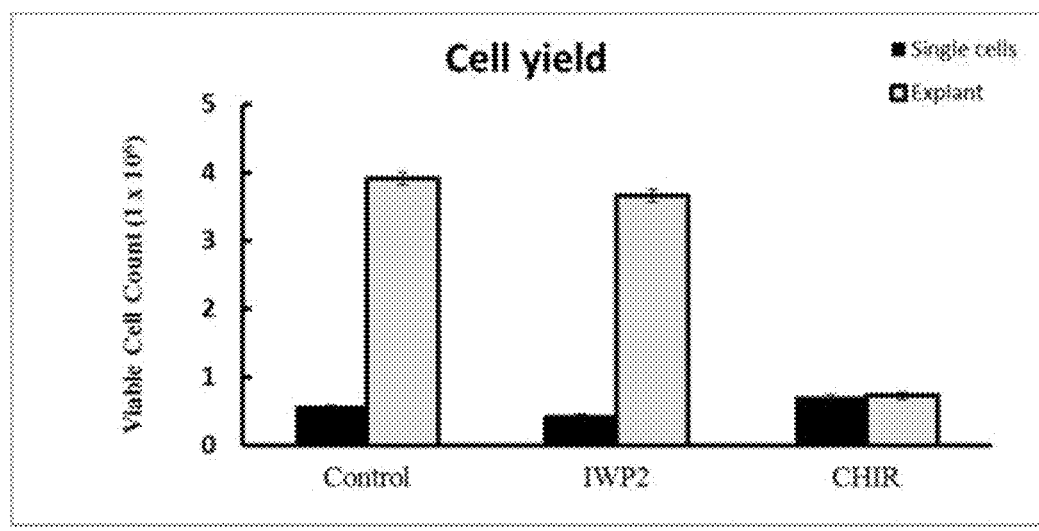
FIG. 6 shows viable cell counts measured after cells harvested from limbal explant outgrowth cultures or isolated limbal epithelial cell cultures are cultured by adding the Wnt inhibitor IWP2 or the Wnt signaling agonist CHIR99021, as a GSK3 inhibitor, to a medium.

As a result, as shown in FIG. 6, in the limbal explant culture, when IWP2 for inhibiting the Wnt/β-catenin signaling was treated, compared with the control, similar yields of viable cells were obtained, whereas under the condition for the single cell culture of limbal tissues, when CHIR99021 was treated, despite the increased $JC1^{low}$ ratio, cell yields were very low, and compared with the control, it also can be seen that the latter is not a suitable method for obtaining LSCs in high yield.

Therefore, it was confirmed that in the limbal explant culture, the inhibition of the Wnt/β-catenin signaling by the Wnt inhibitor treatment can lead to inhibition of LSC differentiation, increase in a CFE, and high yields of LSCs.

When a human limbal explant is cultured using a method according to the present invention, proliferation of LSCs can be improved by inhibiting Wnt/β-catenin signaling, and LSCs can be obtained in high yield by improving the stemness of LSCs. Therefore, when the limbal explant outgrowth sheet is transplanted into an LSCD patient, a successful treatment rate can be increased.

It would be understood by those of ordinary skill in the art that the above descriptions of the present invention are exemplary, and the exemplary embodiments disclosed herein can be easily modified into other specific forms without changing the technical spirit or essential features of the present invention. Therefore, it should be interpreted that the exemplary embodiments described above are exemplary in all aspects, and are not limitative.

What is claimed is:

1. A method for improving the proliferation and maintaining the stemness of limbal stem cells, consisting of:
    (a) immersing in a medium a human limbal explant prepared by placing an epithelial part of a limbal tissue face-up on a polyester membrane insert; and (b) adding a Wnt inhibitor to the medium, thereby improving the proliferation and maintaining the stemness of limbal stem cells,
wherein the Wnt inhibitor is N-(6-Methyl-2-benzothiazolyl)-2-[(3,4,6,7-tetrahydro-4-oxo-3-phenylthieno[3,2-d]pyrimidin-2-yl)thio]-acetamide (IWP2) alone.

2. The method of claim 1, wherein the Wnt inhibitor reduces an amount of β-catenin in cells.

* * * * *